US00PP27146P2

(12) United States Plant Patent
Sills et al.

(10) Patent No.: US PP27,146 P2
(45) Date of Patent: Sep. 13, 2016

(54) BLACKBERRY PLANT NAMED 'DRISBLACKFOURTEEN'

(50) Latin Name: ***Rubus* L. subgenus *Rubus***
Varietal Denomination: DrisBlackFourteen

(71) Applicant: DRISCOLL STRAWBERRY ASSOCIATES, INC., Watsonville, CA (US)

(72) Inventors: Gavin R. Sills, Gilroy, CA (US); Andrea M. Pabon, Gilroy, CA (US); Mark Crusha, Capitola, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 10 days.

(21) Appl. No.: 14/544,846

(22) Filed: Feb. 25, 2015

(51) Int. Cl.
*A01H 5/08* (2006.01)

(52) U.S. Cl.
USPC ..... Plt./203

(58) Field of Classification Search
USPC ..... Plt./203
CPC ..... A01H 5/0887
See application file for complete search history.

*Primary Examiner* — Kent L Bell
(74) *Attorney, Agent, or Firm* — Morrison & Foerster LLP

(57) ABSTRACT

This invention relates to a new and distinct variety of blackberry plant named 'DrisBlackFourteen', particularly characterized by having medium to high yield, medium to large-sized, black berries and self-fruitful plants, is disclosed.

2 Drawing Sheets

Genus and species: *Rubus* L. subgenus *Rubus*.
Variety denomination: 'DrisBlackFourteen'.

BACKGROUND OF THE NEW PLANT

The present invention relates to a new and distinct blackberry cultivar designated 'DrisBlackFourteen' and botanically known as *Rubus* L. subgenus *Rubus*. This new blackberry variety was identified in Santa Cruz County, Calif. in June 2008 and originated from a cross between the proprietary female parent blackberry plant 'BM718.7' (unpatented) and the proprietary male parent blackberry plant 'BN804 (867G1)' (unpatented). The original seedling of the new cultivar was first asexually propagated by tissue culture and root cuttings at a nursery in Santa Cruz County, Calif. in 2008. 'DrisBlackFourteen' was subsequently asexually propagated by tissue culture and root cuttings and underwent further testing at a nursery in Santa Cruz County, Calif. from 2012 to 2014. The present invention has been found to be stable and reproduce true to type through successive asexual propagations.

Plant Breeder's Rights for this variety have not been applied for. 'DrisBlackFourteen' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Santa Cruz County, Calif.

1. Medium to high yield;
2. Medium to large sized, black berries; and
3. Self-fruitful plants.

DESCRIPTION OF THE PHOTOGRAPHS

This new blackberry plant is illustrated by the accompanying photographs which show the plant's canes, flowers, fruit, and leaves. The colors shown are as true as can be reasonably obtained by conventional photographic procedures. The photographs are of plants that are 2 years old.

Figure 1:
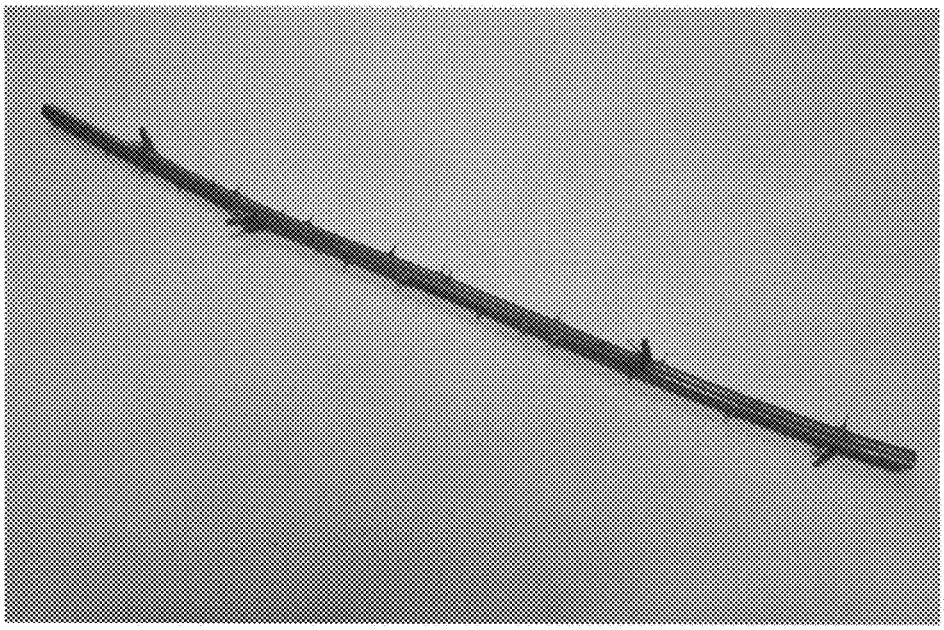
Figure 2:
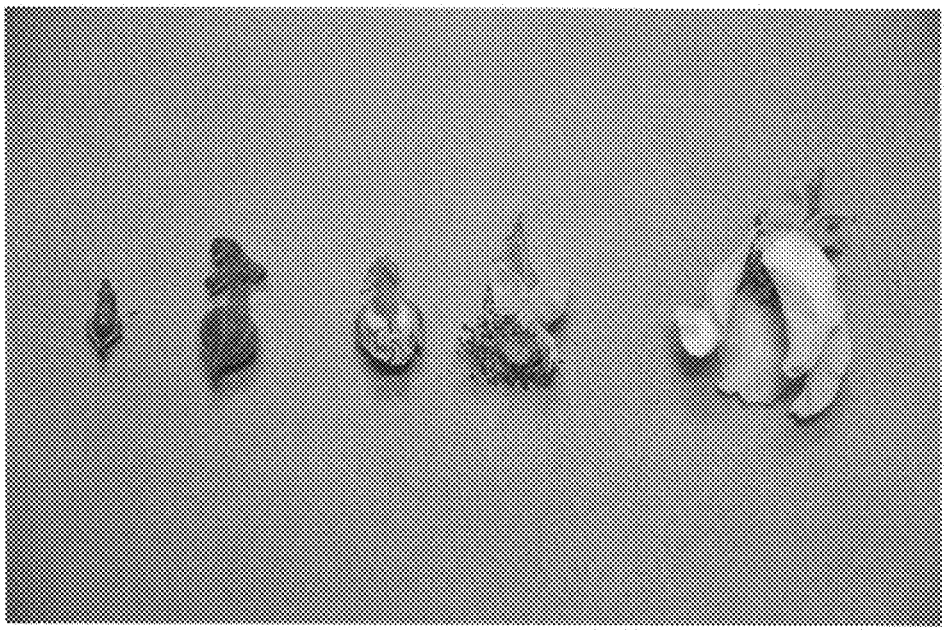
Figure 3:
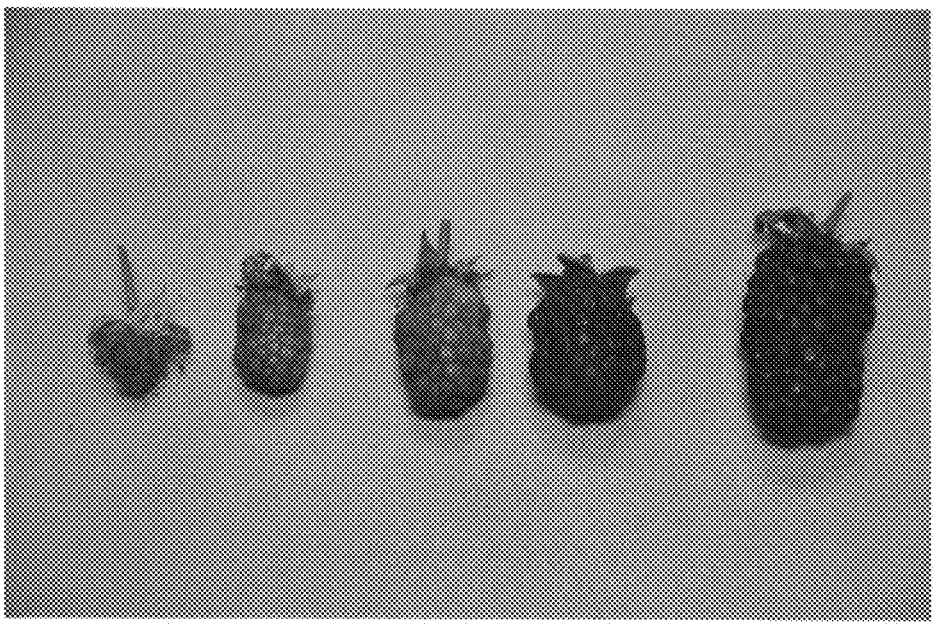
Figure 4:
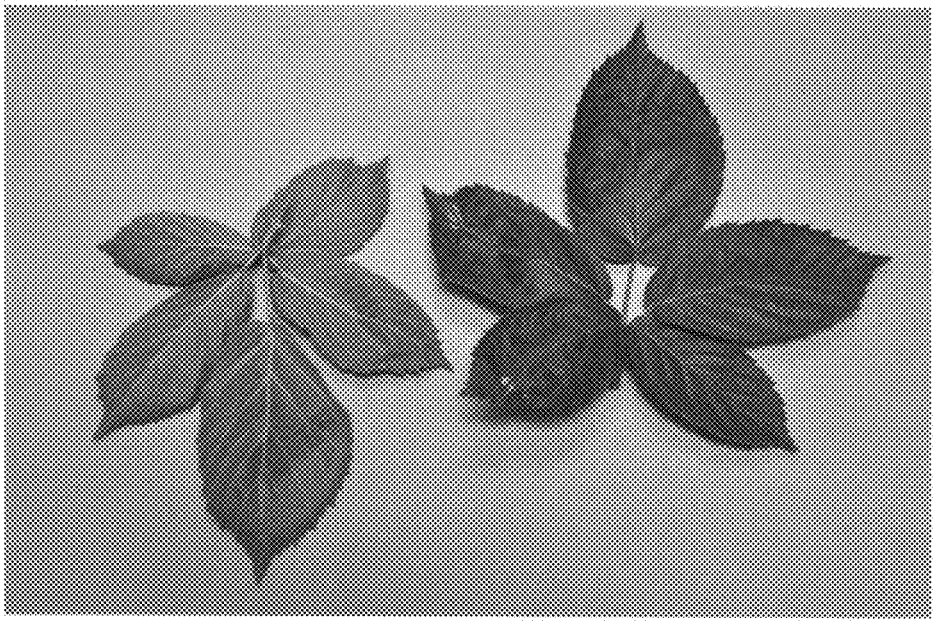

FIG. 1 shows a section of a young cane with spines.
FIG. 2 shows the flowers at various stages.
FIG. 3 shows the fruit at various stages
FIG. 4 shows the upper and lower surfaces of the leaves.

DESCRIPTION OF THE NEW VARIETY

The following descriptions of 'DrisBlackFourteen' are based on observations made in Santa Cruz County, Calif. on 2-year old plants. This description is in accordance with UPOV terminology. Color designations, color descriptions, and other phenotypical descriptions may deviate from the stated values and descriptions depending upon variation in environmental, seasonal, climatic and cultural conditions. 'DrisBlackFourteen' has not been observed under all possible environmental conditions. Color terminology follows The Royal Horticultural Society Colour Chart, London (R.H.S.) (2007 edition). Descriptive terminology is from the *Plant Identification Terminology, An Illustrated Glossary* 2$^{nd}$ edition, by James G. Harris and Melinda Woolf Harris, unless where otherwise defined.

DETAILED BOTANICAL DESCRIPTION

Classification:
- *Family*.—Rosaceae.
- *Botanical*.—*Rubus* L. subgenus *Rubus*.
- *Common name*.—Blackberry.
- *Variety name*.—'DrisBlackFourteen'.

Parentage:
- *Female parent*.—Proprietary blackberry plant named 'BM718.7' (unpatented).
- *Male parent*.—Proprietary blackberry plant named 'BN804 (867G1)' (unpatented).

Plant:

*Vigor*.—Medium to high.

*Growth habit*.—Upright to semi-upright.

*Productivity*.—Medium.

*Propagation*.—Tissue culture and root cuttings.

*Self-fruitfulness*.—Self-fruitful.

*Time of bud burst*.—Late.

Canes:

*Fruiting lateral length* (4$^{th}$ *lateral from tip*).—Medium; 35.9 cm.

*Number of fruit per lateral*.—10.

*Fruiting on current year's cane*.—Present.

*Cane internodal distance*.—5.2 cm.

*Number of new canes during flowering*.—Medium to many.

*New cane strength* (*observed full-grown shoot after picking*).—Medium to strong.

*Glaucosity observed on full-grown shoot after picking*.—Medium.

*Young shoots*.—Quantity: Medium. Time of emergence from soil: Late. Anthocyanin coloration (during rapid growth): Weak; RHS 173A (Medium greyed-orange). Intensity of green color: Medium; RHS 146B (Medium yellow-green). Number of glandular hairs: Medium.

*Dormant cane*.—Length: Medium to long. Diameter (in central third): Medium. Cross section (from mid cane observed at end of first growing season): Rounded to angular. Color: RHS 144B (Medium yellow-green). Number of branches: Medium. Distribution of branches: Only on upper half. Anthocyanin coloration: Medium to strong; RHS 59A (Dark red-purple).

*Spines*.—Quantity: Medium. Size: Medium. Color: RHS 146C (Medium yellow-green). Density (on central third of cane): Medium. Texture: Medium to heavy. Attitude of apex in relation to cane: Outwards.

Leaves:

*Type*.—Palmate.

*Predominant number of leaflets*.—Five.

*Overlapping or relative position of lateral leaflets*.—Overlapping.

*Color*.—Upper surface: Medium; RHS 147B (Medium yellow-green). Lower surface: Medium; RHS 146C (Medium yellow-green).

*Glossiness of upper side*.—Medium.

*Cross section profile*.—Concave (Margins rolled inward).

*Leaflets*.—Shape: Ovate. Margin: Doubly serrate. Depth of incisions: Medium. Type of incision margin: Bi-serrate. Apex: Truncate. Base: Obtuse. Rachis length between terminal leaflet and adjacent lateral leaflet: 53.1 mm.

*Lateral leaflet* (*basal pair*).—Length: 117.5 mm. Width: 86.7 mm. Length/width ratio: 1.4.

*Terminal leaflet*.—Length: Medium; 124.3 mm. Width: Medium; 94.3 mm. Length/width ratio: 1.3. Lobing: Absent. Undulation of margin (rippling of margin): Medium. Blistering between veins (rugosity): Medium. Shape: Ovate. Tip: Complex. Base: Obtuse. Margin: Doubly serrate. Cross-section: V-shaped.

*Petiole*.—Length: 27.9 mm. Diameter: 2.4 mm. Pigmentation: Upper surface: Medium; RHS 146B (Medium yellow-green). Lower surface: Medium; RHS 146C (Medium yellow-green).

*Stipule*.—Size: Small to medium. Orientation: Clasping.

Inflorescence:

*Flower diameter*.—Medium to large; 49.10 mm.

*Flower number* (*at* 3$^{rd}$ node from tip of lateral).—2.

*Petal*.—Length: 24.10 mm. Width: 14.50 mm. Length/width ratio: 1.7. Color: RHS NN155B (White).

*Pedicel*.—Length: 40.10 mm. Diameter: 1.60 mm.

*Time of beginning of flowering on previous year's cane*.—N/A.

*Time of beginning of flowering on current year's cane*.—Late.

Fruit:

*Size*.—Medium to large.

*Length*.—Medium to long; 25.59 mm.

*Width*.—Medium; 21.24 mm.

*Ratio of length to width*.—Medium; 1.2.

*Weight* (*g/fruit*).—6.5 g.

*Soluble solids* (%) (*in Brix*).—10.6.

*Titratable acidity:* (% *as citric acid*).—0.66.

*Seed weight* (*g/seed*).—0.00517.

*Number of drupelets/fruit*.—Medium; 104.9.

*Size of drupelet*.—Medium.

*Color*.—Immature: RHS 145A (Medium green). Maturing: RHS 50A (Medium red). Mature: RHS 203C (Black).

*Firmness*.—Medium.

*Glossiness*.—Weak to medium.

*Shape in longitudinal section*.—Medium ovate.

*Time of ripening on previous year's cane*.—N/A.

*Time of ripening on current year's cane*.—Late.

*Harvest interval*.—Mid-August to mid-November.

*Yield*.—Medium to high.

Disease, pest, and stress resistance:

*Verticillium wilt*.—Susceptible.

COMPARISON WITH PARENTAL AND COMMERCIAL VARIETIES

'DrisBlackFourteen' differs from the proprietary female parent 'BM718.7' (unpatented) in that 'DrisBlackFourteen' has larger fruit and later production than 'BM718.7'.

'DrisBlackFourteen' differs from the proprietary male parent 'BN804 (867G1)' (unpatented) in that 'DrisBlackFourteen' has larger fruit and later production than 'BN804 (867G1)'.

'DrisBlackFourteen' differs from the commercial variety 'DrisBlackNine' (U.S. Plant patent application Ser. No. 14/121,573) in that 'DrisBlackFourteen' has medium ovate shaped fruit that is weakly to medium glossy, whereas 'DrisBlackNine' has oblong shaped fruit that is medium glossy. Additionally, 'DrisBlackFourteen' has a medium number of medium sized drupelets, whereas 'DrisBlackNine' has many small to medium sized drupelets.

'DrisBlackFourteen' differs from commercial variety 'DrisBlackTen' (U.S. Plant Pat. No. 26,611) in that 'DrisBlackFourteen' has medium to large sized fruit that is weakly to medium glossy, whereas 'DrisBlackTen' has large sized fruit that is medium glossy. Additionally, 'DrisBlackFourteen' has a medium to high yield, whereas 'DrisBlackTen' has a low to medium yield.

We claim:

1. A new and distinct variety of blackberry plant named 'DrisBlackFourteen', substantially as illustrated and described herein.

* * * * *